United States Patent [19]

Jensen

[11] Patent Number: 5,246,601
[45] Date of Patent: Sep. 21, 1993

[54] CENTRIFUGATION PROCESS FOR SEPARATING POLYHALOGENATED PRODUCT FROM PRODUCT CENTRATE

[75] Inventor: Wayne D. Jensen, Magnolia, Ark.

[73] Assignee: Ethyl Corporation, Richmond, Va.

[21] Appl. No.: 852,039

[22] Filed: Mar. 16, 1992

[51] Int. Cl.⁵ .................. B01D 21/26; B01D 24/26
[52] U.S. Cl. ............................. 210/787; 210/791; 210/391; 428/303; 428/315.5; 570/186
[58] Field of Search ............... 210/787, 791, 107, 108, 210/380.1, 391, 393, 398, 402; 570/186; 428/303, 315.5

[56] References Cited

U.S. PATENT DOCUMENTS

| | | | |
|---|---|---|---|
| 4,039,450 | 8/1977 | Brown | 210/400 |
| 4,343,700 | 8/1982 | Daubman et al. | 210/380.1 |
| 4,390,427 | 6/1983 | Hünten | 210/391 |
| 5,004,847 | 4/1991 | Beaver et al. | 570/186 |

Primary Examiner—Robert A. Dawson
Assistant Examiner—David Reifsnyder
Attorney, Agent, or Firm—David E. LaRose

[57] ABSTRACT

This invention relates to an improvement in a process for centrifuging a polyhalogenated product, the improvement comprising enhancing the porosity of a centrifuge filter cloth subsequent to one or more centrifugation cycles by effectively treating the centrifuge filter cloth with an amount of filter cloth treatment solution and at a temperature which are sufficient to enhance the centrifuge filter cloth porosity.

25 Claims, No Drawings

CENTRIFUGATION PROCESS FOR SEPARATING POLYHALOGENATED PRODUCT FROM PRODUCT CENTRATE

BACKGROUND

This invention relates to an improved centrifugation method for separating a polyhalogenated product from product centrate or filtrate.

In the production of polyhalogenated flame retardants, well known centrifugation or filtration techniques are typically used to separate the product from the reaction mass and/or slurry containing the product once the halogenation reaction is complete. Typically, the product is a solid which is suspended as a slurry in the reaction mass solvent. Accordingly, the centrifugation cycle should be sufficient to separate the product from the slurry substantially as it is produced without excessive amount of down time for centrifuge cleaning or centrifuge filter cloth replacement. However, due to the particular characteristics of the product and/or slurry being centrifuged, the length of the centrifugation cycle and the number of centrifugation cycles may suffer considerably due to decrease in the porosity of the centrifuge filter cloth. When the filter cloth porosity decreases substantially, centrifugation of the product may decrease to an unacceptable rate. At this point, centrifugation is terminated and corrective action taken. Typically, the appropriate corrective action is changing the filter cloth in order to again increase the product throughput to an acceptable rate. Depending on the size and complexity of the centrifugation equipment, cloth replacement may be quite costly in terms of actual expense and with respect to decrease in production rates. There is a need therefore for a facile economic means for extending the centrifugation cycle for polyhalogenated products in order to decrease the amount of centrifuge down time. For the purposes of this invention, whenever centrifugation is referred to, centrifugation and filtration are contemplated and whenever the term "centrifugation cycle" is used it refers to the number of batches of product that can be centrifuged or a predetermined amount of product that is centrifuged.

SUMMARY OF THE INVENTION

In an effort to increase the number and length of centrifugation cycles between filter cloth changes, and thus decrease centrifuge down time in the production of polyhalogenated products, it has been discovered that centrifuge filter cloth porosity can be substantially enhanced subsequent to one or more centrifugation cycles by effectively treating the filter cloth after removal of the filter cake with an amount of filter cloth treatment solution and at a temperature which are sufficient to enhance the filter cloth porosity. By using the methods of this invention, down time due to the need to replace the centrifuge filter cloth can be substantially reduced and there is less tendency for decrease in centrifuge rates between filter cloth replacements.

Accordingly, the process of this invention may be used for increasing filter cloth porosity for a wide variety of polyhalogenated flame retardant products susceptible to separation from the reaction mass by centrifugation or filtration. The polyhalogenated flame retardant may be substituted with bromine, chlorine, or fluorine, or any combination of two or more of the foregoing. Such flame retardant products may include, without limitation, products predominant in polyhaloalkanes, and cycloalkanes such as dibromoethyldibromocyclohexane, dichloromethyldichlorocyclohexane, hexabromocyclododecane, stabilized hexabromocyclododecane, hexachlorocyclododecane, and the like; products predominant in polyhaloaromatics such as 2,4,6-tribromophenol, tetrabromophthalic acid or anhydride, tetrachlorophthalic acid or anhydride, N,N'-ethylene-(bistetrabromophthalimide), N,N'-ethylene(bistetrachlorophthalimide), tetrabromobisphenol-A, decabromodiphenyl oxide, decabromodiphenylethane, decabromodiphenylmethane, octabromodiphenyl oxide, pentabromodiphenyl oxide, tetradecabromodiphenoxybenzene, ethylenebis(dibromonorbornanedicarboximide), tribromophenyl allyl ether, dibromostyrene, brominated polystyrene, tetrabromophthalate ester, tetrabromobisphenol A-bis(2-hydroxyethyl ether), tetrabromobisphenol A-bis(2,3-dibromopropyl ether), tetrabromobisphenol A-bis(allyl ether), poly-dibromophenylene oxide, bis(tribromophenoxy)ethane, tetrabromophthalate diol, disodium salt of tetrabromophhalate, and the like. Preferably, the process of this invention is used for increasing the porosity of centrifuge filter cloths used in the separation of polyhaloaliphatic flame retardant products from the product centrate, more preferably, polyhalocycloaliphatic flame retardant products, and most preferably a flame retardant product predominant in hexabromocyclododecane.

A critical aspect in the production of polyhalogenated flame retardant products, is the ability to centrifuge the product substantially as it is made. When there is a decrease in the centrifugation rate, due to down time or decrease in filter cloth porosity, the rate of production of the flame retardant product suffers. Thus a key feature of this invention is the ability to substantially enhance the filter cloth porosity after one or more centrifugation cycles. Another feature of this invention, is a reduced frequency of filter cloth changes thus decreasing the amount of centrifuge downtime. Other features of this invention will be evident from the following description and ensuing claims.

DETAILED DESCRIPTION

To substantially enhance the centrifuge filter cloth porosity, the filter cloth after removal of the filter cake is effectively treated with an amount of centrifuge filter cloth treatment solution and at a temperature which are sufficient to enhance the filter cloth porosity. For purposes of this invention, the porosity of the filter cloth is given in terms of the weight in kilograms of product centrifuged per square meter of effective centrifuge filter cloth area per hour. The effective centrifuge filter cloth area is the area of filter cloth which contacts the product and/or centrate during the centrifugation cycle.

The porosity of the centrifuge filter cloth is related to the size of the product particles being centrifuged, the type of filter cloth, the filter cloth pore size or mesh, the temperature of the product being centrifuged, the pressure being applied to force the product through the filter cloth, and whether or not the filter cloth is precoated, among other considerations. When the product being centrifuged is recovered as a solid, it is less desirable to precoat the filter cloth since the product would then have to be separated from the solid precoat material. In the case of polyhalogenated flame retardants, centrifuges or filters preferably do not use filter aid material to precoat the filter cloths since the product is recovered as a solid. In the case of solid polyhalogenated flame retardants, wherein the filter cloths are not precoated, there is a tendency for the porosity of the filter cloths to decrease during each centrifugation cycle. Without desiring to be bound by theory, it is believed that the decrease in filter cloth porosity is due to blinding of the filter cloth with fine particles contained in the product mass being centrifuged. When the filter cloth becomes sufficiently blinded so that the porosity is substantially below that of a new filter cloth, the filter cloth is typically removed from service and a new filter cloth installed. As indicated above, replacement of the filter cloth is not only costly, but results in a decrease in product production rates since the centrifuge is usually removed from service during filter cloth replacement.

Suitable filter cloths for centrifuging polyhalogenated flame retardant products may be formed from polypropylene, teflon, nylon, polyester, metal, or other material which is chemically resistant to the product being centrifuged, and which has a sufficient porosity to allow acceptable centrifugation rates. The mesh or pore size of the filter cloth is desirably substantially smaller than the average size of the particles to be centrifuged. Too large a pore size relative to the particle size will result in product particles plugging the filter cloth pores or loss of product through the filter cloth. Too small a pore size relative to the particles to be centrifuged will result in low filter cloth porosity. For example, in the preparation of hexabromocyclododecane, a major amount of the unfiltered product typically has an average particle size in the range of from about 100 to about 200 microns, with a minor amount of the product having a particle size of less than about 100 microns. Thus a suitable filter cloth would generally have a pore size of less than about 100 microns, preferably less than about 80 microns, and most preferably about 75 microns. In a particularly preferred embodiment, the flame retardant product is hexabromocyclododecane and the filter cloth is a polypropylene filter cloth having a pore size of about 75 microns.

Commonly used filter cloth materials are in the form of felt and monofilament woven synthetic fiber or metal. While felt type filter cloths are generally used for the removal of fine particles from a liquid product, monofilament woven filter cloths provided the advantage of easy release of product solids from the filter cloth. Thus it is highly desirable to utilize a monofilament woven filter cloth in the centrifugation of polyhalogenated flame retardant products and most preferably, monofilament polypropylene filter cloth.

After one or more centrifugation cycles, it is particularly desirable to treat the filter cloth with an amount of treatment solution and at a temperature which are sufficient to substantially increase the filter cloth porosity. By substantially increase is meant to increase the average porosity by more than 20% over the untreated filter cloth average porosity for the same number of centrifugation cycles. Preferably, there will be more than a 50% increase in average porosity, and most preferably more than about a 70% increase in average porosity as compared to average porosity of an untreated filter cloth. The average porosity is determined by measuring the porosity of the filter cloth when first put into service, measuring the filter cloth porosity after a pre-determined number of centrifugation cycles, and obtaining the arithmetic average of the two measured porosities.

Alternatively, the porosity of the filter cloth can be measured after one or more centrifugation cycles, and the arithmetic average porosity obtained.

The treatment solution used in the process of this invention is comprised predominantly of an organic solvent. Suitable organic solvents include aliphatic alcohols such as methanol, ethanol, propanol, butanol, isopropanol, isobutanol, and the like or combinations of two or more of the foregoing; and aromatic hydrocarbon compounds such as benzene, toluene, xylene, and the like or combinations of two or more of the foregoing. Other organic solvents include isobutylisobutyrate, isobutylbromide, acetone, tetrahydrofuran, chloroform, methylene chloride, and the like. By predominant amount is meant more than about 50 percent by weight organic solvent based on the total weight of treatment solution.

When the product to be centrifuged is a polyhaloaliphatic flame retardant, centrate from a previous centrifugation cycle containing a predominant amount of organic solvent is desirably used. In a particularly preferred embodiment, the polyhaloaliphatic flame retardant is hexabromocyclododecane, and the centrate is composed of reaction mass solvent containing a predominant amount of aliphatic alcohol, more preferably a lower aliphatic alcohol, and most preferably, isobutanol.

Typically, the centrate from the production of halogenated flame retardant such as polybromoaliphatic flame retardant contains organic solvent, water, halogen, HBr, partially halogenated aliphatic and cycloaliphatic compounds or any combination of two or more of the foregoing. In a particularly preferred embodiment, the flame retardant is hexabromocyclododecane, and the centrate is a combination of isobutanol, isobutylisobutyrate, isobutylbromide, dissolved brominated isomers of cyclododecatriene, partially brominated cyclododecatriene, HBr, and water with a predominant amount of isobutanol. The amount of isobutanol, isobutylisobutyrate, isobutylbromide, dissolved brominated isomers of cyclododecatriene, HBr, and water in the centrate can vary within wide limits, however, it is particularly desirable that the centrate contain at least about 70 weight percent of isobutanol in order to be effective as a treatment solution.

The amount of water in the centrate is selected to provide the greatest degree of solubility of fine particles which tend to blind the filter cloth. If the water in the centrate is too high, however, there tends to be a decrease in the solubility of the fine particles in the centrate. Therefore, it is preferred that the amount of water in the centrate be less than about 10 percent by weight, more preferably less than about 9 percent by weight and most preferably less than about 7 percent by weight.

Co-organic solvents in the centrate include isobutylisobutyrate and isobutylbromide. The amount of isobutylbromide in the centrate ranges from at least about 0.05 to about 7 weight percent, more preferably from about 0.1 to about 5 weight percent, and most preferably from about 0.2 to about 3.5 weight percent based on the total weight of centrate. The amount of isobutylisobutyrate in the centrate is preferably at least about 0.2 percent by weight, more preferably from about 0.3 to about 7 percent by weight, and most preferably from about 0.5 to about 3.5 percent by weight based on the total weight of centrate. For the purposes of this invention, there may be more or less isobutylbromide and isobutylisobutyrate in the centrate, however it has been found that the preferred ranges of isobutylbromide and isobutylisobutyrate in the centrate provide the production of polyhaloaliphatic flame retardant with the least amount of fine particles when the centrate is recycled as reaction mass solvent to the polyhaloaliphatic flame retardant process.

The centrate may also contain dissolved brominated isomers of cyclododecatriene and a minor amount of hexabromocyclododecane. By minor amount is meant less than about 10 percent by weight based on the total weight of centrate.

The amount of treatment solution used to treat the filter cloth is that amount which is sufficient to effectively increase the average filter cloth porosity to the desired degree. While more treatment solution may be used, it is desirable to only use that amount of treatment solution which is sufficient to achieve a predetermined average filter cloth porosity. Such amount of treatment solution can be determined by a simple trial and error procedure.

When centrate from a previous centrifugation cycle is used as the treatment solution, there is little or no additional load of solvent on the solvent recovery system. This is a particularly key advantage of this invention which advantage is more difficult to achieve if the treatment solution is comprised predominantly of other organic solvents. Furthermore, other organic solvents may be less compatible with the polyhalogenated flame retardant and thus may require disposal rather than recycle to the process wherein the flame retardant product is formed.

Another key feature of the invention is the temperature of the treatment solution. When the treatment solution is comprised of centrate, the temperature of the centrate is preferably maintained above the temperature used for centrifuging the polyhalogenated flame retardant product so as to increase the solubility of fines in the treatment solution. When using centrate from a previous centrifugation cycle, the temperature is typically above room temperature and more preferably above about 40° C. The temperature should not be so high, however, as to cause deformation of the filter cloth during treatment. If the filter cloth is made from metal or teflon, the temperature of the treatment solution may be as high as about 200° C. or higher. In the case of polypropylene filter cloth, it is preferred that the temperature be less than about 100° C., more preferably in the range of from about 55° to about 80° C. and most preferably about 60° to about 75° C., since treatment with treatment solution for extended periods of time at temperatures above about 80° C. may cause an undesirable amount of deformation of the filter cloth.

Temperatures other than the preferred temperatures may be used with other treatment solutions. Accordingly, when the treatment solution is comprised of a more volatile organic solvent such as acetone, chloroform, or methylene chloride, the temperature during contact of the filter cloth with the treatment solution is desirably less than about 40° C., more preferably less than about 30° C. and most preferably from about 0° C. to about 25° C.

The pressure used in treating the filter cloth is not critical to the invention. However, the pressure should be sufficient to adequately contact essentially the entire area of the filter cloth to be treated with the treatment solution. Spray nozzles are typically used to provide the greatest degree of filter cloth contact with the minimum amount of treatment solution. The arrangement of spray nozzles and the pressure required to achieve sufficient contact of the treatment solution with the filter cloth are related to the equipment design and as such are appropriately referred to those skilled in the art.

The following example is given by way of illustration and is not intended to limit the invention in any way.

EXAMPLE I

Hexabromocyclododecane (HBCD) Filtration

CDT is brominated generally in accordance with the procedure disclosed in Jenkner et al. U.S. Pat. No. 3,558,727. Isobutanol containing about 2.5 weight percent water is used as the bromination solvent. The amount of solvent used is that amount which provides a theoretical loading of 50% HBCD particles in the solvent. Commercial batch quantities of product (about 7,000 kilograms of dried product per batch) predominant in HBCD are prepared containing about 50 weight % solids based on the total weight of product and solvent. A centrifuge is used to separate each batch of product solids from the solvent or centrate. The centrifuge was Ametek, Inc. model 48"×30" Batch-O-Matic ® centrifuge having about 3 square meters of filter area. The filter cloth is a polypropylene filter cloth having a pore size of 75 microns, as supplied by Fabricated Filters, Inc. or Ketema, Inc.

Subsequent to centrifuging four batches of product prepared according to the foregoing procedure, the centrifuge filter cloth was treated with about 5300 liters (1400 gallons) of centrate containing 80 wt. % isobutanol, 2 wt. % water, 6 wt. % HBr, 0.3 wt. % isobutyl bromide, 3 wt.% isobutylisobutyrate, and 9 wt. % hexabromocyclododecane isomers of hexabromocyclododecane, and partially brominated cyclododecatriene. The temperature of the centrate during the filter cloth treatment was 60° to 75° C. The treatment solution was pressure fed at 412 KPa (45 psig) to the centrifuge while operating the centrifuge at 1000 revolutions per minute (RPM). By treating the filter cloth after every four batches of product centrifuged, according to the foregoing procedure, the average porosity of the filter cloth after 14 to 25 commercial batches of HBCD predominant product were centrifuged was 1222 kg/hr/m$^2$ (250 lb./hr/ft$^2$).

EXAMPLE II

Comparative Example

HBCD product was prepared generally in accordance with the Example I except that the filter cloth was not treated with the filter cloth treatment solution. After centrifuging seven batches of HBCD product, the average porosity of the filter cloth was 489 kg/hr/m$^2$ (100 lb./hr/ft$^2$).

Variations of the invention are within the spirit and scope of the appended claims.

What is claimed is:

1. In a centrifugation process for separating a substantial amount of polyhalogenated product from product centrate, the improvement comprising enhancing the porosity of a filter cloth subsequent to one or more centrifugation cycles by effectively treating the centrifuge filter cloth after removal of the filter cake with an amount of filter cloth treatment solution an at a temperature which are sufficient to enhance the centrifuge filter cloth porosity.

2. The improvement of claim 1 wherein the polyhalogenated product is hexabromocyclododecane.

3. The improvement of claim 1 wherein the treatment solution is product centrate.

4. The improvement of claim 3 wherein the product centrate is comprised of a predominant amount of isobutanol.

5. The improvement of claim 1 wherein the treatment temperature is less than about 100° C.

6. The improvement of claim 1 wherein the centrifuge filter cloth is monofilament polypropylene filter cloth having about 75 micron pore size.

7. The improvement of claim 1 wherein the enhanced centrifuge filter cloth porosity is greater than about 480 kilograms per hour per square meter of filter cloth area on the average.

8. The improvement of claim 1 wherein the centrifuge filter cloth is treated after four centrifugation cycles.

9. The improvement of claim 1 wherein the temperature is in the range of from about 55° to about 80° C.

10. The improvement of claim 9 wherein the polyhalogenated product is hexabromocyclododecane, and the enhanced centrifuge filter cloth porosity is greater than about 480 kilograms per hour per square meter of filter cloth area on the average.

11. The improvement of claim 10 wherein the treatment solution is product centrate.

12. The improvement of claim 11 wherein the product centrate is comprised of a predominant amount of isobutanol.

13. The improvement of claim 12 wherein the centrifuge filter cloth is treated after four centrifugation cycles.

14. A process for separating a product predominant in hexabromocyclododecane, which process comprises enhancing the porosity of a filter cloth subsequent to one or more centrifugation cycles by effectively treating the centrifuge filter cloth after removal of the filter cake with an amount of filter cloth treatment solution an at a temperature which are sufficient to enhance the centrifuge filter cloth porosity.

15. The process of claim 14 wherein the treatment solution is product centrate.

16. The process of claim 15 wherein the product centrate is comprised of a predominant amount of isobutanol.

17. The process of claim 14 wherein the treatment temperature is less than about 100° C.

18. The process of claim 14 wherein the filter cloth is a polypropylene filter cloth having about 75 micron pore size.

19. The process of claim 14 wherein the enhanced filter cloth porosity is greater than about 480 kilograms per hour per square meter of filter cloth area on the average.

20. The process of claim 14 wherein the filter cloth is treated after four centrifugation cycles.

21. The process of claim 14 wherein the temperature is in the range of from about 55° to about 80° C.

22. The improvement of claim 21 wherein the treatment solution is product centrate.

23. The improvement of claim 22 wherein the centrifuge filter cloth is treated after four centrifuge cycles.

24. The improvement of claim 23 wherein the centrate is comprised of a predominant amount of isobutanol.

25. The improvement of claim 24 wherein the amount of isobutanol in the centrate is at least about 70 percent by weight.

* * * * *